United States Patent
Wang et al.

(10) Patent No.: US 11,236,214 B2
(45) Date of Patent: *Feb. 1, 2022

(54) NUCLEATED C3C4 COPOLYMERS

(71) Applicant: Borealis AG, Vienna (AT)

(72) Inventors: Jingbo Wang, Linz (AT); Wilfried Peter Töltsch, Linz (AT); Luigi Maria Resconi, Linz (AT); Friedrich Berger, Linz (AT)

(73) Assignee: BOREALIS AG, Vienna (AT)

(*) Notice: Subject to any disclaimer, the term of this patent is extended or adjusted under 35 U.S.C. 154(b) by 0 days.

This patent is subject to a terminal disclaimer.

(21) Appl. No.: 16/753,218

(22) PCT Filed: Dec. 18, 2018

(86) PCT No.: PCT/EP2018/085385
§ 371 (c)(1),
(2) Date: Apr. 2, 2020

(87) PCT Pub. No.: WO2019/141462
PCT Pub. Date: Jul. 25, 2019

(65) Prior Publication Data
US 2020/0325303 A1 Oct. 15, 2020

(30) Foreign Application Priority Data
Jan. 22, 2018 (EP) .................. 18152753

(51) Int. Cl.
C08K 5/1575 (2006.01)
A61L 31/04 (2006.01)

(52) U.S. Cl.
CPC ........... C08K 5/1575 (2013.01); A61L 31/048 (2013.01)

(58) Field of Classification Search
CPC combination set(s) only.
See application file for complete search history.

(56) References Cited

U.S. PATENT DOCUMENTS

2016/0046787 A1* 2/2016 Montaletti ........... C08K 5/1575
524/579

FOREIGN PATENT DOCUMENTS

| EP | 1 428 854 | 6/2004 |
|----|-----------|--------|
| EP | 1 614 699 | 1/2006 |
| EP | 1947143 | 7/2008 |
| EP | 2586801 | 1/2013 |
| WO | WO2016/008749 | 1/2016 |

OTHER PUBLICATIONS

International Search Report and Written Opinion for corresponding PCT Application No. PCT/EP2018/085385 dated Jan. 18, 2019.

* cited by examiner

Primary Examiner — Wenwen Cai
(74) Attorney, Agent, or Firm — Fay Sharpe LLP

(57) ABSTRACT

A propylene copolymer composition comprising A) a propylene butylene copolymer which is—free of phthalicacid esters as well as decomposition products thereof; —obtained by a Ziegler-Natta catalyst and B) at least one α-nucleating agent, the propylene copolymer composition having—a MFR (2.16 kg/210° C.) in the range of 2 to 100 g/10 min—a melting point Tm(1) of less than 140° C.—a melting point Tm(2) of at least 150° C., said Tm(2) being associated with more than 75% of the total melting enthalpy and whereby the propylene copolymer—has monomer units derived from a) propylene in an amount of 90.0-98.0 mol.-% b) butylene in an amount of 2.0-10.0 mol.-% with respect to the total weight of the propylene butylene copolymer—an isotacticity mm % as determined by $^{13}$C NMR spectroscopy of below 99.0%; and—a Koenig-B parameter with respect to butylene as determined by $^{13}$C NMR spectroscopy of more than 0.98.

17 Claims, No Drawings

NUCLEATED C3C4 COPOLYMERS

This is a 371 of PCT/EP2018/085385, filed Dec. 18, 2018, which claims priority to European Patent Application No. 18152753.2, filed Jan. 22, 2018, the contents of which are fully incorporated herein by reference.

The present invention relates to nucleated random propylene-butylene polymer compositions, to a process for producing such compositions and further to articles comprising nucleated random propylene-butylene polymer compositions.

BACKGROUND

For polypropylene applications particularly in moulding stiffness of above 1000 MPa is normally required, not only because of requirement from the customer but also for environmental aspects. A material with good stiffness/impact balance not only provides that the article meets the application requirements, but also allows down gauging, which will reduce the energy consumption and C02 emission. For PP homopolymer, generally the stiffness is related to the crystallinity, which is controlled by the chain regularity. Polymer chains with higher regularity induce a faster crystallization of the whole material and make lamellae thicker, which is beneficial to stiffness.

In general terms, in a PP copolymer, the co-monomer reduces the isotactic sequence length, and as a consequence, reduces the thickness of the crystalline lamellae, therefore reducing the stiffness. The same effect is generated by stereoerrors in the propylene sequences. In the case of propylene-1-butene copolymers, the 1-butene comonomer reduces stiffness less that in the case of, for example, ethylene or 1-hexene. The randomness of both stereorerrors and co-monomer units, both intra-molecular and inter-molecular, is very important to define the material properties balance.

In a further aspect, many propylene-butylene copolymers have been prepared by high yield Ziegler-Natta catalyst systems (so called fourth and fifth generation type), which comprises a catalyst component, a co-catalyst component and an internal donor based on phthalate-compositions; typical examples for such catalysts being disclosed in U.S. Pat. No. 5,234,879, WO92/19653, WO 92/19658 and WO 99/33843. However, some of these phthalate-compositions are under suspicion of generating negative health and environmental effects. Furthermore, the market simply asks for "phthalate-free polypropylene" suitable for various applications, e.g. in the field of packaging and medical applications as well as personal care, or personal hygiene.

Traditional catalysts have been used in WO2016025326 reporting the preparation of C3C4C2 terpolymers in the presence of polyvinylcyclohexane (PVCH). Similarly WO2007096209 reports the preparation of proypylene copolymers with traditional Ziegler or Metallocene catalysts having moderately high melting points and being produced in two sequential gas phase reactors.

Recently catalysts with citraconate as internal donor have attracted interest.

WO2017/001479 discloses a polymerization process for obtaining C3C4 copolymers or C3C4C2 terpolymers with a Ziegler Natta catalyst using preferably citraconate as internal donor and tert-alkyl-methoxysilanes as external donor. The co- and terpolymers are prepared by autoclave reactors, used for film but have relatively low melting points.

WO2017/001474 also discloses a polymerization process for obtaining C3C4 copolymers or C3C4C2 terpolymers with a Ziegler Natta catalyst using preferably citraconate as internal donor and iso-propyl-methoxysilanes as external donor. The co- and terpolymers prepared with the phthalate free catalyst system showed poor melting points.

WO2016/198601 also discloses a polymerization process for obtaining C3C4 copolymers or C3C4C2 terpolymers with a Ziegler Natta catalyst using preferably citraconate as internal donor and dicyclopentyldimethoxysilane (donor D) as external donor in two reactors coupled in series. Again the C6 solubles (FDA) indicated room for improvement.

WO 2012/007430 is one example of a limited number of patent applications, describing phthalate free catalysts based on citraconate as internal donor.

Thus in addition to the above well-known conflict of aims there is also the conflict of providing a "phthalate free material" having some amorphous part reflected by a second melting point, a first relatively high melting point and simultaneously extremely low C6(FDA) extractability, and excellent impact strength/stiffness ratio.

SUMMARY OF THE INVENTION

The present invention is based on the finding that the above mentioned object can be achieved by preparing a propylene butylene copolymer with a specific Ziegler Natta catalyst free of phthalic acid ester using at least one alpha nucleating agent.

The present invention insofar provides a propylene copolymer composition comprising
A) a propylene butylene copolymer which is
  free of phthalic acid esters as well as decomposition products thereof;
  obtained by a Ziegler-Natta catalyst and
B) at least one α-nucleating agent,
the propylene copolymer composition having
  a MFR (2.16 kg/210° C.) in the range of 2 to 100 g/10 min
  a melting point Tm(1) of less than 140° C.
  a melting point Tm(2) of at least 150° C., said Tm(2) being associated with more than 75% of the total melting enthalpy and whereby the propylene copolymer
  has monomer units derived from
a) propylene in an amount of 90.0-98.0 mol.-%
b) butylene in an amount of 2.0-10.0 mol.-% with respect to the total weight of the propylene butylene copolymer
  an isotacticity mm % as determined by 13C NMR spectroscopy of below 99.0%; and
  a Koenig-B parameter with respect to butylene as determined by 13C NMR spectroscopy of more than 0.98

The present invention further provides
a process for the preparation of a propylene butylenes copolymer composition comprising
A) a propylene butylene copolymer which is
  free of phthalic acid esters as well as decomposition products thereof; and
B) at least one α-nucleating agent,
the propylene copolymer composition having
  a MFR (2.16 kg/210° C.) in the range of 2 to 100 g/10 min
  a melting point Tm(1) of less than 140° C.
  a melting point Tm(2) of at least 150° C., said Tm(2) being associated with more than 75% of the total melting enthalpy
whereby the propylene copolymer
has monomer units derived from
a) propylene in an amount of 90.0-98.0 mol.-%
b) butylene in an amount of 2.0-10.0 mol.-% with respect to the total weight of the propylene butylene copolymer,
the process comprising polymerizing propylene and butylene in a sequential polymerization process,
in the presence of a Ziegler Natta catalyst system including Ziegler Natta catalyst Basell Avant ZN180M and further including an organosilane as external donor, preferably dicyclopentyl dimethoxysilane (donor D), cyclohexyl trimethoxysilane (donor C) or tert.butyl dimethoxy(methyl) silane (donor T3) and triethylaluminium as cocatalyst,
whereby in a first reactor a pre-polymerization is carried out at 25-35° C. yielding a pre-polymer,
further polymerizing the pre-polymer
  at a temperature of 65-75° C.
  at a C4/C3 ratio of 115 to 145 mol/kmol yielding a first intermediate having an C4 content of 4 to 7 wt.-%,
transferring the first intermediate to a second reactor and further polymerizing—at a temperature of 75 to 90° C.
  at a C4/C3 ratio of 90 to 130 mol/kmol,
to yield the second reactor product,
optionally further polymerizing the second reactor product in a third reactor,
  at a temperature of 75 to 90° C.
  at a C4/C3 ratio of 70 to 100 mol/kmol,
extruding the second reactor product or if present the third reactor product in the presence of an alpha nucleating agent to yield the propylene butylene copolymer composition, whereby the amount of alpha nucleating agent is less than 0.25 wt.-% with respect to the total of the composition.

In yet a further aspect the present invention is concerned with products as obtained from this process and articles made from the inventive compositions.

From a general point of view the present invention provides compositions with a unique balance of C6(FDA), stiffness, NIS and also haze.

Definitions

A propylene butylene polymer composition according to the present invention is derived from propylene and butylenes monomer units. It is self-evident that traces of other monomers such as from nucleating agents can be present. Traces means less than 0.5 wt.-% with respect to the total propylene butylene copolymer composition.

A propylene butylenes copolymer obtained by a Ziegler-Natta catalyst means that the propylene butylenes copolymer is obtained by polymerizing propylene and butylenes in the presence of a Ziegler Natta catalyst.

"Free of phthalic acid esters as well as decomposition products thereof" indicates absence of such components within the well accepted understanding in the art.

"Free of phthalic acid esters as well as decomposition products thereof" indicates a maximum of 10 μg/kg, i.e. 10 ppb by weight. Such values have been reported for common soil and river sediments. It is well known for many years that the actual detection limit is lower than the environmental background concentration. Attention is drawn to H. Fromme, T. Küchler, T. Otto, K. Pilz, J. Müller, A. Wenzel Water Research 36 (2002) 1429-1438 which is incorporated by reference herewith. Detection is straightforward by gas chromatography coupled with one- or two-dimensional mass spectrometry (GC-MS respectively GC-MS/MS) optionally preceded by enrichment on a suitable adsorption material.

A Ziegler Natta catalyst system includes the solid Ziegler Natta catalyst component (SC), the external donor and the co-catalyst. Ziegler Natta catalyst system and Ziegler Natta polymerization catalyst are used interchangeable.

By definition, in isotactic polymers all substituents at pseudo-asymmetric C atoms are located on the same side of the macromolecular backbone. Isotacticity of the polyproylenes of the present invention is determined by $^{13}$C-NMR and given as triade percentage (mm %).

The Koenig B-value describes the distribution of the butylenes comonomer along the polymer chain. Koenig B values can range from 0 to 2 whereby 1 designates a perfectly random distribution of comonomer units. The higher the Koenig B value, the more alternating the comonomer distribution in the copolymer. The lower the Koenig B value, the more blocky or clustered the comonomer distribution in the copolymer. The Koenig B value is known in the art for many years and is determined as described in Jack L. Koenig, Spectroscopy of Polymers, 2nd Ed., Elsevier, 1999).

B is defined for a propylene/ethylene copolymer as:

$$B = f(PP+PB)/(2 \cdot F_{PP} \cdot F_{PB})$$

Whereby
f (PP+PB) is the sum of the PP and PB diad fractions; and
$F_{PP}$ is the mole fraction of the propylene in the copolymer
$F_{PB}$ is the mole fraction of the butylene in the copolymer The propylene polymer compositions according to the present invention are produced in a sequential polymerization process. The term "sequential polymerization process" indicates that the propylene polymer composition is produced in at least two reactors connected in series.

DETAILED DESCRIPTION

The composition according to the present invention necessarily include at least one alpha nucleating, preferably a sorbitol derivative alpha nucleating agent and most preferably 1,3:24-Bis (3,4-dimethylobenzylideno) sorbitol (DMDBS).

It is essential for the inventive compositions that the comprised propylene butylenes copolymers do not contain phthalic acid esters as well as decomposition products thereof. As defined above "Free of phthalic acid esters as well as decomposition products thereof" indicates a maximum of 10 μg/kg, i.e. 10 ppb by weight. This is guaranteed by the use of a Ziegler Natta catalyst not having a phthalate internal donor for the preparation. In other words, the catalyst used in the present invention is a Ziegler-Natta catalyst comprising a specific solid catalyst component (SC) free of phthalic acid esters or derivates thereof. It is further particularly preferred that the propylene butylenes polymer composition is free of phthalic acid esters as well as decomposition products thereof, i.e. the composition as a whole meets the maximum of 10 μg/kg, i.e. 10 ppb by weight. In other words any further component being within the scope of the claims due to the comprising wording also has to meet the criteria as set forth above.

The propylene polymer composition according to the present invention has a melt flow rate MFR2 (2.16 kg load, 230° C.) measured according to ISO 1133, in the range of 2 to 100 g/10 min, preferably in the range of 3 to 75 g/10 min, more preferably in the range of 5 to 50 g/10 min, especially in the range of 6 to 45 g/10 min.

Melting temperatures (Tm) and crystallization temperatures (Tc) are measured according to ISO 11357-3. The propylene copolymer composition according to the present invention has to have at least two melting points denoted Tm(1) and Tm(2). Tm(1) as a matter of definition denotes the lower temperature melting point of the at least two melting points present. Tm(1) has to be less than 140° C., preferably in the range of 120 to 138° C., more preferably 122 to 136° C. and most preferably 124 to 136° C. It is assumed the presence of such melting point indicates the presence of some minor amount of softer material contributing to the good impact properties.

Tm(2) is at least 150° C., preferably at least 151° C. and more preferably at least 151° C. to 159° C. It is further required said melting point Tm(2) is associated with more than 75% of the total melting enthalpy following ISO11357-3:2001. Preferably said melting point Tm(2) is associated with more than 78% to 96%, more preferably 80% to 95% of the total melting enthalpy following ISO11357-3:2001. Such relatively high melting temperature ensures high temperature stability as desirable for sterilization in the field of medical and food packing applications.

The propylene butylenes copolymer according to the present invention contains monomer units derived from
a) propylene in an amount of 90.0-98.0 mol.-%
b) butylene in an amount of 2.0-10.0 mol.-%
with respect to the total weight of the propylene butylene copolymer.

Preferably the propylene butylenes copolymer according to the present invention contains monomer units derived from
a) propylene in an amount of 91.0-97.5 mol.-%
b) butylene in an amount of 2.5-9.0 mol.-%
with respect to the total weight of the propylene butylene copolymer.

Most preferably the propylene butylenes copolymer according to the present invention contains monomer units derived from
a) propylene in an amount of 92.0-97.0 mol.-%
b) butylene in an amount of 3.0-8.0 mol.-%
with respect to the total weight of the propylene butylene copolymer.

The isotacticity (as mm %) as determined by 13C NMR spectroscopy is below 99.0%, preferably within the range of 95.0 to 98.5% and most preferably 96.5 to 98.0%.

The Koenig B parameter with respect to butylene as determined by 13C NMR spectroscopy is more than 0.98, preferably more than 0.99 and most preferably 1.00 to 1.04. This indicates the butylenes comonomer has a nearly perfect random distribution with the tendency of marginally more alternating.

The xylene soluble fraction (XCS) of the propylene polymer composition according to the present invention is less than 7.0 wt.-%. Preferably the xylene soluble fraction (XCS) of the propylene polymer composition according to the present invention ranges from 2.0 wt.-% to less 6.0 wt.-% and most preferably 2.5 wt.-% to less than 5.5 wt.-%.

The composition according to the present invention preferably has a content of hexane hot solubles C6(FDA) of less than 1.5 wt.-%, more preferably 0.20 wt. % to 1.20 wt. % and most preferably 0.25 to 1.00 wt. %. Such exceptional low values allow applicability in a broad field of applications including the medical field and also food packaging.

The composition according to the present invention is further preferably characterized by a low ratio of (content of hexane hot solubles C6(FDA))/(xylene soluble fraction (XCS)) [wt.-%/wt.-%] of below 0.25, preferably 0.10 to 0.20 and most preferably 0.10 to 0.19. The ratio indicates the exceptional low of hexane hot solubles C6(FDA) for a given XCS. This is particularly important as good levels of impact are accompanied by the presence of some low crystalline material as reflected by XCS. The low ratio of (content of hexane hot solubles C6(FDA))/(xylene soluble fraction (XCS)) [wt.-%/wt.-%] indicates that the inventive compositions have addressed the conflict of aims of having low C6 extractability and at the same time desirable residual XCS guaranteeing good impact.

In yet a further aspect, the inventive compositions usually have a flexural modulus of 1200 to 1700 MPa, preferably from 1200 to 1650 MPa, and most preferably from 1250 to 1600 MPa.

The composition according to the present invention preferably has a Tc as measured by DSC as described in the experimental part of above 117° C., preferably 118° C. to 128° C. and most preferably 118° C. to 127° C.

In a further aspect the composition according to the present invention preferably has a notched impact strength (NIS, 23° C.) of at least 3.5 kJ/m$^2$, preferably from 4.0 to 12.0 kJ/m$^2$.

The composition according to the present invention preferably further has a haze (1 mm) of below 20%, more preferably below 16% and most preferably below 14%.

In the following the process according to the present invention for providing the compositions according to the present invention shall be described in more detail.

The process according to the present invention for the preparation of a propylene butylenes copolymer composition according to the present invention comprising
A) a propylene butylene copolymer which is
    free of phthalic acid esters as well as decomposition products thereof; and
B) at least one α-nucleating agent,
the propylene copolymer composition having
    a MFR (2.16 kg/210° C.) in the range of 2 to 100 g/10 min
    a melting point Tm(1) of less than 140° C.
    a melting point Tm(2) of at least 150° C., said Tm(2) being associated with more than 75% of the total melting enthalpy
whereby the propylene copolymer
has monomer units derived from
a) propylene in an amount of 90.0-98.0 mol.-%
b) butylene in an amount of 2.0-10.0 mol.-%
with respect to the total weight of the propylene butylene copolymer, the process comprising polymerizing propylene and butylene in a sequential polymerization process,
in the presence of a Ziegler Natta catalyst system including Ziegler Natta catalyst Basell Avant ZN180M and further including an organosilane as external donor, preferably dicyclopentyl dimethoxysilane (donor D), cyclohexyl trimethoxysilane (donor C) or tert.butyl dimethoxy(methyl) silane (donor T3) and triethylaluminium as cocatalyst,
whereby in a first reactor a pre-polymerization is carried out at 25-35° C. yielding a pre-polymer,
further polymerizing the pre-polymer
    at a temperature of 65-75° C.
    at a C4/C3 ratio of 115 to 145 mol/kmol yielding a first intermediate having an C4 content of 4 to 7 wt.-%,
transferring the first intermediate to a second reactor and further polymerizing—at a temperature of 75 to 90° C.
    at a C4/C3 ratio of 90 to 130 mol/kmol,
to yield the second reactor product,
optionally further polymerizing the second reactor product in a third reactor,
    at a temperature of 75 to 90° C.
    at a C4/C3 ratio of 70 to 100 mol/kmol,
extruding the second reactor product or if present the third reactor product in the presence of an alpha nucleating agent to yield the propylene butylene copolymer composition, whereby the amount of alpha nucleating agent is less than 0.25 wt.-% with respect to the total of the composition.

The Ziegler Natta catalysts useful for the inventive process are commercially available for example from Lyondell-Basell under the Avant ZN trade name, whereby Avant ZN180M is the most suitable commercially available catalyst.

The Ziegler-Natta catalyst (ZN-C) is used in association with an alkyl aluminum cocatalyst (Co) and an external donor (ED) being an organosilane. It is preferred to use an organo silane of the general formula

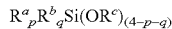
$$R^a_p R^b_q Si(OR^c)_{(4-p-q)}$$

wherein $R^a$, $R^b$ and $R^c$ denote a hydrocarbon radical, in particular an alkyl or cycloalkyl group, and wherein p and q are numbers ranging from 0 to 3 with their sum p+q being equal to or less than 3. $R^a$, $R^b$ and $R^c$ can be chosen independently from one another and can be the same or different. Specific examples of such organo silanes are (tert-butyl)$_2$Si(OCH$_3$)$_2$, (cyclohexyl)(methyl)Si(OCH$_3$)$_2$, (phenyl)$_2$Si(OCH$_3$)$_2$ and (cyclopentyl)$_2$Si(OCH$_3$)$_2$, or of general formula

$$Si(OCH_2CH_3)_3(NR^3R^4)$$

wherein $R^3$ and $R^4$ can be the same or different a represent a hydrocarbon group having 1 to 12 carbon atoms.

$R^3$ and $R^4$ are independently selected from the group consisting of linear aliphatic hydrocarbon group having 1 to 12 carbon atoms, branched aliphatic hydrocarbon group having 1 to 12 carbon atoms and cyclic aliphatic hydrocarbon group having 1 to 12 carbon atoms. It is in particular preferred that $R^3$ and $R^4$ are independently selected from the group consisting of methyl, ethyl, n-propyl, n-butyl, octyl, decanyl, iso-propyl, iso-butyl, iso-pentyl, tert.-butyl, tert.-amyl, neopentyl, cyclopentyl, cyclohexyl, methylcyclopentyl and cycloheptyl.

More preferably both $R^1$ and $R^2$ are the same, yet more preferably both $R^3$ and $R^4$ are an ethyl group.

Especially preferred external donors (ED) are the dicyclopentyl dimethoxy silane donor (D-donor), the cyclohexylmethyl dimethoxy silane donor (C-Donor) and the tert-butyl dimethoxy(methyl)silane (donor T3).

In addition to the Ziegler-Natta catalyst (ZN-C) and the external donor (ED), a co-catalyst (Co) is used. The co-catalyst (Co) is preferably triethylaluminium (TEAL). Other co-catalysts may also be used upon adaptation.

Optionally the Ziegler-Natta catalyst (ZN-C) can be modified by the so called BNT-technology during the above described pre-polymerization step in order to introduce a further polymeric nucleating agent, preferably a vinyl polymer derived from monomers of the formula

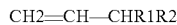
$$CH_2=CH-CHR1R2$$

wherein R1 and R2 are alkyl and may form a ring. Most preferably the polymeric nucleating agent is vinylcyclohexane.

The compositions according to the present invention can be made in small quantities in a prepolymerization plus bulk polymerization sequence.

In such prepolymerization plus bulk polymerization sequence process propylene and butylene are preferably polymerized in the presence of a Ziegler Natta catalyst system including Ziegler Natta catalyst Basell Avant ZN180M and further including an organosilane as external donor, preferably selected from the group of dicyclopentyl dimethoxysilane (donor D), cyclohexyl trimethoxysilane (donor C) or tert.butyl dimethoxy(methyl)silane (donor T3), and triethylaluminium as cocatalyst, whereby in a first reactor a pre-polymerization is carried out at 15-25° C. for 5 to 15 minutes yielding a pre-polymer, further polymerizing the pre-polymer in a bulk reactor at a temperature of 65-75° C.

at an average C4/(C4+C3) weight ratio of 15 to 25 wt. %; and a residence time of 45 to 75 minutes yielding a reactor product; and extruding the reactor product in the presence of an alpha nucleating agent to yield the propylene butylene copolymer composition, whereby the amount of alpha nucleating agent is less than 0.25 wt.-% with respect to the total of the composition. The average C4/(C4+C3) weight ratio (in percent) pertains to the liquid phase.

However, the propylene polymer compositions according to the present invention are preferably produced in a sequential polymerization process. The term "sequential polymerization process" indicates that the propylene polymer composition is produced in at least two reactors connected in series.

In one preferred embodiment the term "sequential polymerization process" indicates in the present application that the polymer of the first reactor (R-1), i.e. the propylene homo- or co-polymer fraction (A), is directly conveyed with unreacted monomers to the second reactor (R-2) in which the propylene butylenes copolymer fraction (B) is produced.

Accordingly, a decisive aspect of the present process is the preparation of the propylene polymer composition in at least two separate reactors, wherein the reaction mixture of the first reactor (R-1) is conveyed, preferably directly conveyed, to the second reactor (R-2), and thus the propylene polymer compositions comprise two fractions, namely fractions (A) and (B). Accordingly, the present process comprises at least a first reactor (R-1) and a second reactor (R-2).

The process may preferably comprise at least one additional polymerization reactor (R-3) subsequent to reactor (R-2).

The term "polymerization reactor" indicates a reactor, where the main polymerization takes place. Thus in case the process consists of two or more polymerization reactors, this definition does not exclude the option that the overall process comprises for instance a pre-polymerization step in a pre-polymerization reactor. The term "consists of" is only a closing formulation in view of the main polymerization reactors. In case the process configuration comprises a pre-polymerization reactor, fraction (A) means the sum of (co)polymers produced in the pre-polymerization reactor and in the first polymerization reactor (R-1).

The polymerization reactors are selected from slurry and gas phase reactors.

The first reactor (R-1) is preferably a slurry reactor (SR) and can be any continuous or simple stirred batch tank reactor or a loop reactor operating in bulk or slurry. By "bulk polymerization" is meant a process, where the polymerization is conducted in a liquid monomer essentially in the absence of an inert diluent. However, as it is known to a person skilled in the art, the monomers used in commercial production may contain aliphatic hydrocarbons as impurities. For instance, the propylene monomer may contain up to 5% of propane as an impurity. Thus, preferably polymerization in bulk means polymerization in a reaction medium that comprises of at least 60% (wt/wt) of the monomer. According to the present invention the slurry reactor (SR) is preferably a (bulk) loop reactor (LR).

The second reactor (R-2) is preferably a gas phase reactor (GPR). Such gas phase reactor (GPR) can be any mechanically mixed or fluidized bed reactor or settled bed reactor. The third reactor (R-3) is preferably a gas phase reactor (GPR). Again such gas phase reactor (GPR) can be any mechanically mixed or fluidized bed reactor or settled bed reactor.

Preferably the gas phase reactor (GPR) comprises a mechanically agitated fluidized bed reactor with gas velocities of at least 0.2 m/sec. The gas phase reactor of a fluidized bed type reactor can further include a mechanical agitator to facilitate the mixing within the fluidized bed.

A preferred sequential polymerization process is a "loop-gas phase"-process, such as developed by Borealis (known as BORSTAR@ technology) described e.g. in patent literature, such as in WO-A-98/58976, EP-A-887380 and WO-A-98/58977.

Preferably in the first reactor (R-1), preferably in the slurry reactor (SR), like in the loop reactor (LR), the temperature is equal or more than 65° C., preferably in the range of equal or more than 67° C. to equal or below 75° C., still more preferably in the range of equal or more than 67° C. to equal or below 74° C. The pressure in the first reactor (R-1), preferably in the slurry reactor (SR), like in the loop reactor (LR), is not a critical issue, however, is typically within the range of 4000 to 6500 kPa.

Hydrogen can be added into the reactor for controlling the molar mass in a manner known per se.

Subsequently, the reaction mixture from the first reactor (R-1) is transferred to the second reactor (R-2), i.e. to the gas phase reactor (GPR-1), whereby the temperature in the second reactor (R2) is preferably within the range of equal or more than 75° C. to equal or below 85° C., more preferably of equal or more than 77° C. to equal or below 82° C.

Further it is preferred that in the second reactor (R-2), preferably in the gas phase reactor (GPR-1), the pressure is within the range of 2000 to 4000 kPa. Hydrogen can be added for controlling the molar mass in a manner known per se.

The residence time can vary in both reactor zones.

If a third reactor (R-3) is used, preferably a second gas phase reactor, (GPR-2) the preferred temperature and preferred pressures ranges are the same as given above for the second reactor (R-2), particularly the first gas phase reactor (GPR-1).

In one embodiment of the process for producing propylene butylenes polymer compositions of the present invention the residence time in the bulk reactor, e.g. loop reactor, is in the range 0.2 to 2 hours, preferably 0.3 to 1.0 hour and the residence time in gas phase reactor (GPR-1) will generally be 0.75 to 3.0 hours, preferably 1.0 to 2.0 hours more preferably 1.25 to 2.0 hours. In a second preferred embodiment including the use of three reactors coupled in series, it is preferred that the polymerization in the further gas phase reactor, preferably the second gas phase reactor (GPR-2) is operated at a residence time of 1 minute to 45 minutes, preferably 1 to 10 minutes.

The present process encompasses a pre-polymerization (Pr) prior to the polymerization in the first reactor (R-1). The pre-polymerization (Pr) can be conducted in the first reactor (R-1), however it is often preferred in commercial processes that the pre-polymerization (Pr) takes place in a separate reactor, so called pre-polymerization reactor (Pr-R). A pre-polymerization reactor is of smaller size compared to the first (R-1) and second (R-2) reactor, respectively. The reaction volume of the pre-polymerization reactor (Pr-R) can be e.g. between 5% and 40% of the reaction volume of the first reactor (R-1), like the loop reactor. In said pre-polymerization reactor (Pr-R), the pre-polymerization (Pr) is performed in bulk or slurry as defined for the first reactor (R-1) above.

Further the pre-polymerization temperature is rather low, i.e. usually 25 to 35° C.

Residence times for prepolymerization can vary between 0.1 to 1.0 hours, like between 0.2 and 0.6 hours, typically 15 to 30 minutes.

The amount of polymer material made in the first reactor, preferably the loop reactor, preferably is 30 to 70 wt.-% including also the minor amount of polymer material made in pre.polymerization.

More preferably the amount is 40 to 65 wt.-%. If only two reactor are used (pre-polymerization is not considered insofar), the amount preferably will be in the upper end, i.e. preferably will be 45 to 60 wt.-%. If three reactors are used the amount preferably will be 40 to 55 wt.-%. As known in the art the amount of material is also referred to as split.

The amount of polymer material made in the second reactor, preferably the first gas phase reactor, preferably is 30 to 70 wt.-%. If only two reactor are used (pre-polymerization is not considered insofar), the amount preferably will be 40 to 55 wt.-%. If three reactors are used the amount preferably will be 35 to 50 wt.-%.

The amount of polymer material made in the third reactor, preferably the second gas phase reactor, preferably is less than 25 wt.-%, more preferably less than 20 wt.-% and most preferably less than 15 wt.-%.

According to the process of the invention butylene comonomer can be fed independently into the polymerization process. A feed of butylenes to all three reactors nevertheless is preferred.

Feeding butylenes and ethylene comonomer independently into the polymerization process means that it is possible that both are fed to the same reactor(s) or are fed into different reactors.

It is preferred to purge the polymer after the polymerization to reduce the amount of residual hydrocarbons in the polymer. Typically the purging step is conducted in a purge vessel where the polymer is contacted with a purge gas, conventionally nitrogen. The temperature during the purging step is from 30 to 110° C., preferably from 30 to 95° C. and more preferably from 40 to 80° C. The average residence time is from 5 to 240 minutes, preferably from 10 to 200 minutes. Catalyst residues are deactivated with steam or moisturized air.

Preferably the purging step is conducted continuously. In a preferred embodiment the polymer particles are introduced to the top of the purge vessel and removed from the bottom. Thereby a downward flow of polymer particles is established. The purge gas is typically introduced at the bottom of the purge vessel so as to achieve a counter-current flow of particles and gas. The gas flow is selected so that no fluidization of the polymer particles occurs in the purge vessel. Thereby a narrow residence time distribution of the polymer particles is obtained and the process has a good efficiency.

The A/Ti ratio of the catalyst system is preferably within the range of 185 to 220 mol/mol, preferably 190 to 210 mol/mol.

The external donor/Ti ratio preferably is in the range of 7 to 13 mol/mol, more preferably 8 to 12 mol/mol.

The product as obtained from the reactor or reactor sequence is extruded in the presence of an alpha nucleating agent in an amount of less than 0.25 wt.-% with respect to the total weight of the composition. Preferably the amount of alpha nucleating agent is from 0.10 to 0.22 wt.-%.

As used herein the term "moulded article" is intended to encompass articles that are produced by any conventional moulding technique, e.g. injection moulding, stretch moulding, compression moulding, rotomoulding or injection stretch blow moulding. The term is not intended to encompass articles that are produced by casting or extrusion, such as extrusion blow moulding. Thus the term is not intended to include films or sheets.

The present invention is also concerned with compositions as obtained from the process as described above.

In yet a further aspect, the present invention is concerned with articles produced by injection moulding, stretch moulding, or injection stretch blow moulding are preferred. Articles produced by injection moulding are especially preferred.

The articles preferably are thin-walled articles having a wall thickness of 300 micrometer to 2 mm. More preferably the thin-walled articles have a wall thickness of 300 micrometer to 1400 micrometer, and even more preferably the thin-walled articles have a wall thickness of 300 micrometer to 900 micrometer.

The articles of the current invention can be containers, such as cups, buckets, beakers, trays or parts of such articles, such as see-through-windows, lids, or the like.

The articles of the current invention are especially suitable for containing food, especially frozen food, such as ice-cream, frozen liquids, sauces, pre-cooked convenience products, and the like.

Articles of the current invention are also suitable for medical or diagnostic purposes, such as syringes, beaker, pipettes, etc.

It is however envisaged in the present invention, that the articles made of the inventive compositions may comprise further ingredients, such as additives (stabilizers, lubricants, colorants) or polymeric modifiers. It is particularly preferred the amount of polymeric modifiers is limited to 5 wt.-% of the total material.

EXAMPLES

Measurement Methods

MFR2 (230° C.) is measured according to ISO 1133 (230° C., 2.16 kg load).

Phthalic Acid Esters and Decomposition Products

Detection is carried out by gas chromatography coupled with one- or two-dimensional mass spectrometry (GC-MS respectively GC-MS/MS) optionally preceded by enrichment on a suitable adsorption material.

"Free of phthalic acid esters as well as decomposition products thereof" indicates a maximum of 10 μg/kg, i.e. 10 ppb by weight.

Typical equipment to be used is for example given in H. Fromme, T. Küchler, T. Otto, K. Pilz, J. Müller, A. Wenzel Water Research 36 (2002) 1429-1438 which is incorporated by reference herewith.

Description of Quantitative $^{13}$C NMR Spectroscopy

Quantitative nuclear-magnetic resonance (NMR) spectroscopy was used to quantify the comonomer content of the polymers.

Quantitative $^{13}$C{$^{1}$H} NMR spectra recorded in the molten-state using a Bruker Advance III 500 NMR spectrometer operating at 500.13 and 125.76 MHz for $^{1}$H and $^{13}$C respectively. All spectra were recorded using a $^{13}$C optimised 7 mm magic-angle spinning (MAS) probehead at 180° C. using nitrogen gas for all pneumatics. Approximately 200 mg of material was packed into a 7 mm outer diameter zirconia MAS rotor and spun at 4 kHz. This setup was chosen primarily for the high sensitivity needed for rapid identification and accurate quantification (Klimke 2006, Parkinson 2007, Castignolles2009) Standard single-pulse excitation was employed utilising the NOE at short recycle delays (Pollard 2004, Klimke 2006) and the RS-HEPT decoupling scheme (Fillip 2005, Griffin 2007). A total of 16384 (16 k) transients were acquired per spectra using a 3 s recycle delay.

Quantitative $^{13}$C{$^{1}$H} NMR spectra were processed, integrated and relevant quantitative properties determined from the integrals. All chemical shifts are internally referenced to the methyl isotactic pentad (mmmm) at 21.85 ppm.

Basic Comonomer Content Method Spectral Analysis Method Characteristic signals corresponding to the incorporation of 1-butene were observed and the comonomer content quantified in the following way.

The amount 1-butene incorporated in PPBPP isolated sequences was quantified using the integral of the αB2 sites at 43.6 ppm accounting for the number of reporting sites per comonomer:

$$B = I\alpha/2$$

The amount of 1-butene incorporated in PPBBPP double consecutively sequences was quantified using the integral of the ααB2B2 site at 40.5 ppm accounting for the number of reporting sites per comonomer:

$$BB = 2*I\alpha\alpha$$

When double consecutive incorporation was observed the amount of 1-butene incorporated in PPBPP isolated sequences needed to be compensated due to the overlap of the signals αB2 and αB2B2 at 43.9 ppm:

$$B = (I\alpha - 2*I\alpha\alpha)/2$$

The total 1-butene content was calculated based on the sum of isolated and consecutively incorporated 1-butene:

$$B\text{total} = B + BB$$

The amount of propene was quantified based on the main Sαα methylene sites at 46.7 ppm and compensating for the relative amount of αB2 and αB2B2 methylene unit of propene not accounted for (note B and BB count number of butane monomers per sequence not the number of sequences):

$$P\text{total} = I_S\alpha\alpha + B + BB/2$$

The total mole fraction of 1-butene in the polymer was then calculated as:

$$fB = (B\text{total}/(B\text{total} + P\text{total})$$

The full integral equation for the mole fraction of 1-butene in the polymer was:

$$fB = (((I\alpha - 2*I\alpha\alpha)/2) + (2*I\alpha\alpha))I_S\alpha\alpha + ((I\alpha - 2*I\alpha\alpha)/2) + ((2*I\alpha\alpha)/2)) + ((I\alpha - 2*I\alpha\alpha)/2) + (2*I\alpha\alpha))$$

This simplifies to:

$$fB = (I\alpha/2 + I\alpha\alpha)/(I_S\alpha\alpha + I\alpha + I\alpha\alpha)$$

The total comonomer incorporation of 1-butene in mole percent was calculated from the mole fraction in the usual manner:

$$B[\text{mol \%}] = 100*fB$$

The total comonomer incorporation of 1-butene in weight percent was calculated from the mole fraction in the standard manner:

$$B[\text{wt \%}] = 100*(fB*56.11)/((fB*56.11) + ((1-fB)*42.08))$$

Comonomer dyad sequences determination

Comonomer sequence distribution was quantified at the dyad level using the same characteristic signals and integrals as used previously. The constitutive equations were:

$$PP=I_S\alpha\alpha$$

$$PB=I\alpha$$

$$BB=I\alpha\alpha$$

Note that for simplicity the two indistinguishable reversible PB and BP dyads are termed PB i.e. PB=PB+BP. The mole fraction of each dyad was determined through normalisation to the sum of all dyads $$XX=PP+PB+BB$$

$$fPP=PP/XX$$

$$fPB=PB/XX$$

$$fBB=BB/XX$$

The total mole fraction of 1-butene in the polymer was determined from the dyad distribution in the usual way:

$$fB=fBB+fPB/2$$

The full integral equation for the mole fraction of 1-butene in the polymer was:

$$fB=(I\alpha\alpha+\alpha/2)/(I_S\alpha\alpha+I\alpha+I\alpha\alpha)$$

Note this equation is identical to that determined from the basic comonomer content quantification method.

$$fP=1-fB$$

Sequence Order Parameter Description and Quantification

Sequence order parameter, Sequence order parameter, $\chi$ as it is defined by Koenig (Koenig 1992) (or "Koenig B-value" as it is named in WO 2010/078479 A1), yields information about whether the distribution of the structures is random, i.e. can be described by Bernoullian statistics, and whether it tends towards an alternating or block distribution. This parameter can be determined by the formula:

$$B_{Koenig}=fPB/(2*fB*fP)$$

Tacticity Distribution and Isotacticity Quantification

The triad tacticity distribution was determined through direct separate integration of each methyl signals in a region between 23.6-19.7 (Busico 2001, Busico 1997) from a given steric triad followed by normalisation to the sum of methyl signal from all steric triads. Characteristic signals corresponding to regio-defects were not observed {resconi00}. The relative content of a specific steric triad is reported as the mole fraction or percentage of a given steric triad xx with respect to all steric triads:

$$[xx]=xx/(mm+mr+rr)$$

The triad isotacticity was thus given by:

$$[mm]=mm/(mm+mr+rr)$$

When appropriate integrals were corrected for the presence of sites not directly associated with steric triads.

Average Sequence Length Determination

The average length of stereo sequences consisting of two or more monomer unites with like tacticity accounting for the presence of comonomer, i.e. the comonomer corrected meso sequence length determined from the triad tacticity distribution (MSL2'), was calculated using the mole fractions of the mm and mr steric triads and mole fraction of the butene content accounting for both isolated and consecutively incorporated:

$$Bcomp=B*((PB/2)/((PB/2)+BB))$$

$$MSL2'=(((1-([Bcomp]*3))*[mm])/(((1-([Bcomp]*3))*0.5*[mr])+[Bcomp]))+2$$

It should be noted that if no consecutive double incorporation is observed Bcomp becomes B. If no signals due to comonomer insertions are observed Bcomp becomes zero and equation for MSL2' is identical to that for MSL2 (MSL2=2+2 [mm]/[mr]).

REFERENCES FOR $^{13}$C-NMR SPECTROSCOPY

Jack. L Koenig, Spectroscopy of Polymers, American Chemical Society, Washington, D.C. 1992

Busico, V., Cipullo, R., Monaco, G., Vacatello, M., Segre, A. L., Macromoleucles 30 (1997) 6251

Resconi, L., Cavallo, L., Fait, A., Piemontesi, F., Chem. Rev. 2000, 100, 1253

Busico, V., Cipullo, R., Prog. Polym. Sci. 26 (2001) 443

Pollard, M., Klimke, K., Graf, R., Spiess, H. W., Wilhelm, M., Sperber, O., Piel, C., Kaminsky, W., Macromolecules 2004; 37:813.

Filip, X., Tripon, C., Filip, C., J. Mag. Resn. 2005, 176, 239

Klimke, K., Parkinson, M., Piel, C., Kaminsky, W., Spiess, H. W., Wilhelm, M., Macromol. Chem. Phys. 2006; 207:382.

Busico, V., Carbonniere, P., Cipullo, R., Pellecchia, R., Severn, J., Talarico, G., Macromol. Rapid Commun. 2007, 28, 1128

Griffin, J. M., Tripon, C., Samoson, A., Filip, C., and Brown, S. P., Mag. Res. in Chem. 200745, S1, S198

Parkinson, M., Klimke, K., Spiess, H. W., Wilhelm, M., Macromol. Chem. Phys. 2007; 208:2128.

Zhou, Z., Kuemmerle, R., Qiu, X., Redwine, D., Cong, R., Taha, A., Baugh, D. Winniford, B., J. Mag. Reson. 187 (2007) 225

Castignolles, P., Graf, R., Parkinson, M., Wilhelm, M., Gaborieau, M., Polymer 50 (2009) 2373

Melting and Crystallisation Temperature

The melting and crystallisation temperature $T_m$ and $T_c$ are determined according to ISO 11357-1, -2 and -3 with a TA-Instruments 2920 Dual-Cell with RSC refrigeration apparatus and data station. A heating and cooling rate of 10° C./min is applied in a heat/cool/heat cycle between +23 and +210° C., the crystallisation temperature Tc being determined in the cooling step and the Tm melting temperature being determined in the second heating step.

Xylene Cold Soluble fraction at room temperature (XCS, wt.-%) is determined at 25° C. according to ISO 16152; 5th edition; 2005 Jul. 1.

C6 (FDA)

Hexane solubles (wt.-%): determined in accordance with FDA section 177.1520 1 g of a polymer cast film of 100 pin thickness (produced on a PM30 cast film line using chill-roll temperature of 40° C.) is extracted by 400 ml hexane at 50° C. for 2 hours while stirring with a reflux cooler. After 2 hours the mixture is immediately filtered on a filter paper No 41. The precipitate is collected in an aluminium recipient and the residual hexane is evaporated on a steam bath under N2 flow. The precipitate was weighted again and hexane solubles were calculated.

Notched Impact Strength

The Charpy notched impact strength (NIS) was measured according to ISO 179 1 eA at +23° C., using injection molded bar test specimens of 80×10×4 mm³ prepared in accordance with EN ISO 1873-2.

Haze

Haze is determined according to ASTM D1003-00 on 60×60×1 mm³ plaques injection molded in line with EN ISO 1873-2

Flexural Modulus

Flexural Modulus was determined in three-point bending according to ISO 178 using 80×10×4 mm³ test bars injection molded in line with EN ISO 1873-2.

Material Description:

Catalyst

Commercial catalyst Basell Avant ZN180M was used for all inventive examples IE1 to IE4.

In these Examples, the external donor D (Dicyclopentyl dimethoxy silane CAS 126990-35-0) was used.

Cocatalyst component used was triethylaluminium.

For the comparative examples a Ziegler Natta catalyst with a phthalate internal donor and T3 (tert.butyl dimethoxy (methyl)silane CAS 18293-81-7) as the external donor was used.

Polymerization

The polymerization conditions are listed in the Table below.

Examples IE1 to IE4 were stabilized with 0.1 wt.-% of Irganox B225 (1:1-blend of Irganox 1010 and Irgafos 168) of BASF AG, Germany), 0.05 wt.-% calcium stearate.

2000 ppm Millad 3988 (1,3:2,4 Bis(3,4-dimethylbenzylidene) sorbitol) was used as the alpha nucleating agent.

The mixture of polymer and additives was extruded to pellets by using a PRISM TSE16, L/D ratio of screw is 25 extruder under nitrogen atmosphere and final polymer properties were measured.

Comparative Examples CE1 and 2 were stabilized with 0.1 wt.-% of Irganox B225 (1:1-blend of Irganox 1010 and Irgafos 168) of BASF AG, Germany), 0.05 wt.-% calcium stearate 2000 ppm Millad 3988 (1,3:2,4 Bis(3,4-dimethylbenzylidene) sorbitol) was used as the alpha nucleating agent for the comparative example.

The mixture of polymer and additives was extruded under nitrogen atmosphere and final polymer properties were measured.

IE1, IE2, CE1 and CE2 were prepared in a bench scale reactor. IE3 and IE4 were made in a pilot reactor configuration. For IE1 and IE2 the A/Ti ratio (mol/mol) was 200 and the Al/external donor ratio was 10 (mol/mol). Prepolymerization was carried out at 20° C. Residence time was 10 min. The prepolymer was further polymerized in a bulk polymerization at a temperature of 70° C. at an average calculated C4/(C4+C3) weight ratio of 0.21 w % (IE1) and 0.30 w % (IE2) respectively. Average calculated C4/C3 weight ratio in the liquid phase was 0.26 g/g and 0.44 g/g. Residence time was 60 min. Hydrogen feed was adapted to meet the target melt flow rates. The comparative examples were made in an analogous way, i.e. using the same sequence of prepolymerization and bulk polymerization, as well as same reaction temperatures and residence times.

|  |  | IE1<br>IE1 | IE2<br>IE2 | CE1 | CE2 |
|---|---|---|---|---|---|
| Catalyst | type | Avant ZN180M | Avant ZN180M | Phthalate containing ZN catalyst | Phthalate containing ZN catalyst |
| Donor | type | D | D | T3 | T3 |
| Composition* |  |  |  |  |  |
| MFR 230° C./2.16 kg | g/10 min | 9 | 12 | 14 | 12 |
| C4 | mol % | 3.7 | 5.9 | 5.8 | 8.7 |
| mm(NMR) | % | 97.7 | 97.8 | 98.4 | 98.4 |
| Koenig-B(NMR) | — | — | 1.02 | 1.01 | 0.98 | 0.96 |
| Tm, 1(DSC) | ° C. | 135 | 128 | 129 | 128 |
| Tm, 2(DSC) | ° C. | 154 | 151 | 151 | 147 |
| Hm, 2(DSC, rel.) | % | 87 | 90 | 42 | 43 |
| Tc(DSC) | ° C. | 122 | 119 | 120 | 117 |
| XCS | wt % | 3.2 | 4.0 | 2.4 | 3.6 |
| C6(pharm) | wt % | 0.42 | 0.73 | 0.47 | n.m. |
| C6/XCS | — | 0.13 | 0.18 | 0.19 | — |
| Flexural mod. | MPa | 1508 | 1312 | 1301 | 1151 |
| NIS 23° C. | kJ/m² | 4.6 | 5.8 | 5.2 | 5.8 |
| Haze (1 mm) | % | 12 | 9 | 14 | 16 |

*All compositions nucleated with 0.2 wt % DMDBS (Millad 3988); stabilization as described above It can be seen the inventive compositions have lower haze and a better NIS/flexural modulus balance meaning that for a given stiffness (i.e. flexural modulus) the NIS is higher.

IE3 and IE4 were made in a loop/GPR configuration

|  |  | IE3 | IE4 |
|---|---|---|---|
| Catalyst | type | Avant ZN180 M | Avant ZN180 M |
| Ext. donor | type | D | D |
| Al/external donor | mol/mol | 10 | 10 |
| Al/Ti ratio | mol/mol | 200 | 200 |
| Prepoly |  |  |  |
| Temperature | ° C. | 20 | 20 |
| R1 (Loop1) |  |  |  |
| Temperature | ° C. | 70 | 70 |
| Pressure | kPa | 5500 | 5500 |
| Residence time | h | 0.4 | 0.4 |
| Split | wt % | 52 | 52 |
| H2/C3 ratio | mol/kmol | 2.9 | 3.1 |
| C4/C3 ratio | mol/kmol | 121 | 123 |
| R2 (GPR1) |  |  |  |
| Temperature | ° C. | 80 | 80 |
| Pressure | kPa | 2700 | 2700 |
| Residence time | h | 1.75 | 1.73 |
| Split | wt % | 48 | 48 |
| H2/C3 ratio | mol/kmol | 36.1 | 39.1 |
| C4/C3 ratio | mol/kmol | 110 | 112 |

The invention claimed is:

1. A propylene copolymer composition comprising
A) a propylene butylene copolymer which is
   free of phthalic acid esters as well as decomposition products thereof; and
   obtained by a Ziegler-Natta catalyst;
and
B) at least one α-nucleating agent,
the propylene copolymer composition having
   a MFR (2.16 kg/210° C.) in the range of 2 to 100 g/10 min and
   a melting point Tm(1) of less than 140° C. and
   a melting point Tm(2) of at least 150° C., said Tm(2) being associated with more than 75% of the total melting enthalpy;
and whereby the propylene butylene copolymer has monomer units derived from
   a) propylene in an amount of 90.0-98.0 mol.-% and
   b) butylene in an amount of 2.0-10.0 mol.-%
   with respect to the total weight of the propylene butylene copolymer; and
   an isotacticity mm % as determined by 13C NMR spectroscopy of below 99.0%; and
   a Koenig-B parameter with respect to butylene as determined by $^{13}$C NMR spectroscopy of more than 0.98.

2. The composition of claim 1 comprising less than 0.25 wt.-% of the at least one alpha nucleating agent with respect to the total weight of the composition.

3. The composition of claim 1 having a xylene soluble content (XCS) of below 7.0 wt.-% determined at 25° C. according to ISO 16152; 5$^{th}$ edition 2005-07-01.

4. The composition of claim 1 having a content of hexane hot solubles C6(FDA) of less than 1.5 wt.-%.

5. The composition of claim 1, whereby the composition has a flexural modulus of 1200 to 1650 MPa.

6. The composition of claim 1 having a ratio hot solubles C6(FDA)/xylene soluble (XCS) of 0.10 to 0.20.

7. The composition of claim 1 having a flexural modulus of 1200 to 1700 MPa determined in three-point bending according to ISO 178 using 80×10×4 mm$^3$ test bars injection molded in line with EN ISO 1873-2.

8. The composition of claim 1 whereby the propylene butylene copolymer has a Tc as measured by DSC of above 117° C.

9. The composition of claim 1 having a notched impact strength of above 3.5 kJ/m$^2$ measured according to ISO 179 1eA at +23° C. using injection molded bar test specimens of 80×10×4 mm$^3$ prepared in accordance with EN ISO 1873-2.

10. The composition of claim 1 having a haze (1 mm) of below 20% determined according to ASTM D1003-00 on 60×60×1 mm$^3$ plaques injection molded in line with EN ISO 1873-2.

11. An article made from the composition according to claim 1.

12. A sequential polymerization process for the preparation of the propylene copolymer composition of claim 1, comprising:
   polymerizing propylene and butylene in a first reactor at 25-35° C. in the presence of a Ziegler Natta catalyst system including a Ziegler Natta catalyst, an organosilane as external donor, and triethylaluminium as cocatalyst, yielding a pre-polymer,
   further polymerizing the pre-polymer
      at a temperature of 65-75° C. and
      at a C4/C3 ratio of 115 to 145 mol/kmol yielding a first intermediate having an C4 content of 4 to 7 wt.-%,
   transferring the first intermediate to a second reactor and further polymerizing
      at a temperature of 75 to 90° C. and
      at a C4/C3 ratio of 90 to 130 mol/kmol,
   to yield the second reactor product,
   optionally further polymerizing the second reactor product in a third reactor,
      at a temperature of 75 to 90° C. and
      at a C4/C3 ratio of 70 to 100 mol/kmol, and
   extruding the second reactor product or if present a third reactor product from the third reactor in the presence of an alpha nucleating agent to yield the propylene copolymer composition,
   whereby the amount of alpha nucleating agent is less than 0.25 wt.-% with respect to the total of the propylene copolymer composition.

13. The process of claim 12, wherein the organosilane is dicyclopentyl dimethoxysilane, cyclohexyl trimethoxysilane, or tert.butyl dimethoxy(methyl)silane.

14. A composition as obtained from the process according to claim 12.

15. A sequential polymerization process for the preparation of the propylene copolymer composition of claim 1, comprising:
   polymerizing propylene and butylene in a first reactor at 15-25° C. for 5 to 15 minutes in the presence of a Ziegler Natta catalyst system including a Ziegler Natta catalyst, an organosilane as external donor, and triethylaluminium as cocatalyst, yielding a pre-polymer,
   further polymerizing the pre-polymer in a bulk reactor
      at a temperature of 65-75° C. and
      at an average C4/(C4+C3) weight ratio of 15 to 25 wt. %; and
      a residence time of 45 to 75 minutes yielding a reactor product; and
   extruding the reactor product in the presence of an alpha nucleating agent to yield the propylene copolymer composition, whereby the amount of alpha nucleating agent is less than 0.25 wt.-% with respect to the total of the propylene copolymer composition.

16. The process of claim 15, wherein the organosilane is dicyclopentyl dimethoxysilane, cyclohexyl trimethoxysilane, or tert.butyl dimethoxy(methyl)silane.

17. A composition as obtained from the process according to claim 15.

* * * * *